(12) United States Patent
Belliveau et al.

(10) Patent No.: US 7,588,707 B2
(45) Date of Patent: Sep. 15, 2009

(54) MULTILAYERED ARTICLES HAVING BIOCOMPATIBILITY AND BIOSTABILITY CHARACTERISTICS

(75) Inventors: Brian P. Belliveau, Sandown, NH (US); Robert B. Downie, Woburn, MA (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 11/846,678

(22) Filed: Aug. 29, 2007

(65) Prior Publication Data

US 2007/0292649 A1   Dec. 20, 2007

Related U.S. Application Data

(62) Division of application No. 10/694,681, filed on Oct. 28, 2003, now Pat. No. 7,264,858.

(60) Provisional application No. 60/422,032, filed on Oct. 29, 2002.

(51) Int. Cl.
B29C 47/06 (2006.01)

(52) U.S. Cl. .............................. 264/177.14; 264/209.1; 264/171.26

(58) Field of Classification Search ............... 264/171.1, 264/171.12, 171.26, 173.16, 177.14, 209.1; 428/36.91
See application file for complete search history.

(56) References Cited

U.S. PATENT DOCUMENTS

| | | | |
|---|---|---|---|
| 3,411,981 A | 11/1968 | Thomas | |
| 4,131,731 A | 12/1978 | Lai et al. | |
| 4,211,741 A | 7/1980 | Ostoich | |
| 4,303,457 A | 12/1981 | Johansen et al. | |
| 4,447,590 A | 5/1984 | Szycher | |
| 4,523,005 A | 6/1985 | Szycher | |
| 4,789,720 A | 12/1988 | Teffenhart | |
| 4,798,597 A | 1/1989 | Vaillancourt | |
| 4,874,360 A | 10/1989 | Goldberg et al. | |
| 5,449,022 A | 9/1995 | Witthaus et al. | |
| 5,712,044 A | 1/1998 | Fanselow et al. | |
| 5,730,919 A | 3/1998 | Wilfong et al. | |
| 5,733,619 A | 3/1998 | Patel et al. | |
| 5,738,902 A | 4/1998 | Forrestal et al. | |
| 5,738,923 A | 4/1998 | Ko et al. | |

(Continued)

FOREIGN PATENT DOCUMENTS

DE    4022741 A1    1/1992

(Continued)

OTHER PUBLICATIONS

ASTM Designation D2240-95, "Standard Test Method for Rubber Property-Durometer Hardness", 1995, pp. 403-406.

(Continued)

*Primary Examiner*—Thao T. Tran
(74) *Attorney, Agent, or Firm*—Joe A. Powell; Samuel B. Laferty; Thoburn T. Dunlap

(57) ABSTRACT

Multilayer articles, such as tubing and films, are disclosed which have a soft layer of aliphatic polyurethane and at least one layer of hard aliphatic polyurethane. The articles formed avoid the problem of tackiness when using only a soft aliphatic polyurethane, while maintaining flexibility. The articles are also biocompatible and biostable and are suitable for use in medical applications.

3 Claims, 2 Drawing Sheets

U.S. PATENT DOCUMENTS

| | | |
|---|---|---|
| 5,993,436 A | 11/1999 | Kitou et al. |
| 6,127,043 A | 10/2000 | Lange |
| 6,392,002 B1 | 5/2002 | Wu |
| 6,431,219 B1 | 8/2002 | Redler et al. |

FOREIGN PATENT DOCUMENTS

| | | |
|---|---|---|
| DE | 20303982 U1 | 5/2003 |
| GB | 2111067 A | 6/1983 |
| JP | 2117403 A | 5/1990 |

OTHER PUBLICATIONS

Article on "Tecoflex MG Physical Test Data", Thermedics Polymer Products, a division of VIASYS Healthcare, no date, one page.

Article on "Technical Information", Thermedics Polymer Products, a division of VIASYS Healthcare, Dec. 2001, pp. 1-10.

Article on "Biocompatibility/Biostability", Thermedics Polymer Products, a division of VIASYS Healthcare, no date, 9 pages.

Article on "Processing Information", Thermedics Polymer Products, a division of VIASYS Healthcare, Dec. 2001, pp. 1-7.

U. Frieden et al., NeoResins, The Netherlands, "New Developments of Solvent Based Polyurethane Resins for Printing Inks", 6 pages.

MULTILAYERED ARTICLES HAVING BIOCOMPATIBILITY AND BIOSTABILITY CHARACTERISTICS

CROSS-REFERENCE

This patent application is a division of U.S. Pat. No. 7,264,858 issued on Sep. 4, 2007, which claims priority to Provisional Application Ser. No. 60/422,032 filed on Oct. 29, 2002.

BACKGROUND OF THE INVENTION

Polyvinylchloride (PVC) is an accepted material for use as tubing in various medical applications and is commonly used as tubing in food processing, particularly for fluids and semi-solids. PVC polymer chains form an attraction to one another, which produces a very rigid plastic. When a soft or flexible plastic is required, a plasticizer may be added to allow the chains to slide against each other. Phthalates may be used as a plasticizer for PVC medical and surgical products, such as a IV tubes, blood bags, and ventilation tubes.

It is believed that phthalate does not bind to the PVC, remaining present as a freely mobile and leachable phase in the plastic. It is also believed that phthalates migrate out of the PVC polymer, since it is not bound to the PVC molecule. When used in medical tubing, phthalate has been found to accumulate in blood, lung, and liver tissue, as well as in fat. These plasticizers may have ill effects on humans, and in particular, children.

SUMMARY OF THE INVENTION

The invention includes a multilayered article comprising a first layer of soft polyurethane having an inner and outer surface and at least one second layer of hard polyurethane on at least one of the inner and outer surface. The soft and hard polyurethanes are aliphatic polyurethanes and are polyether or polycarbonate based, that is, the polyol used to produce the polyurethane is either a polyether or polycarbonate. The polyurethanes used in this invention are biocompatible and biostable and thus the articles made are suitable for medical applications.

The invention also involves a process for producing the articles by coextrusion or solution casting.

BRIEF DESCRIPTION OF THE DRAWINGS

The accompanying drawings, which are incorporated herein and constitute a part of this specification, illustrate the presently preferred embodiments of the invention and, together with the general description given above and the detailed description given below, serve to explain the features of the invention. The drawings are not shown to scale.

In the drawings.

DESCRIPTION OF THE INVENTION

Figure 1:
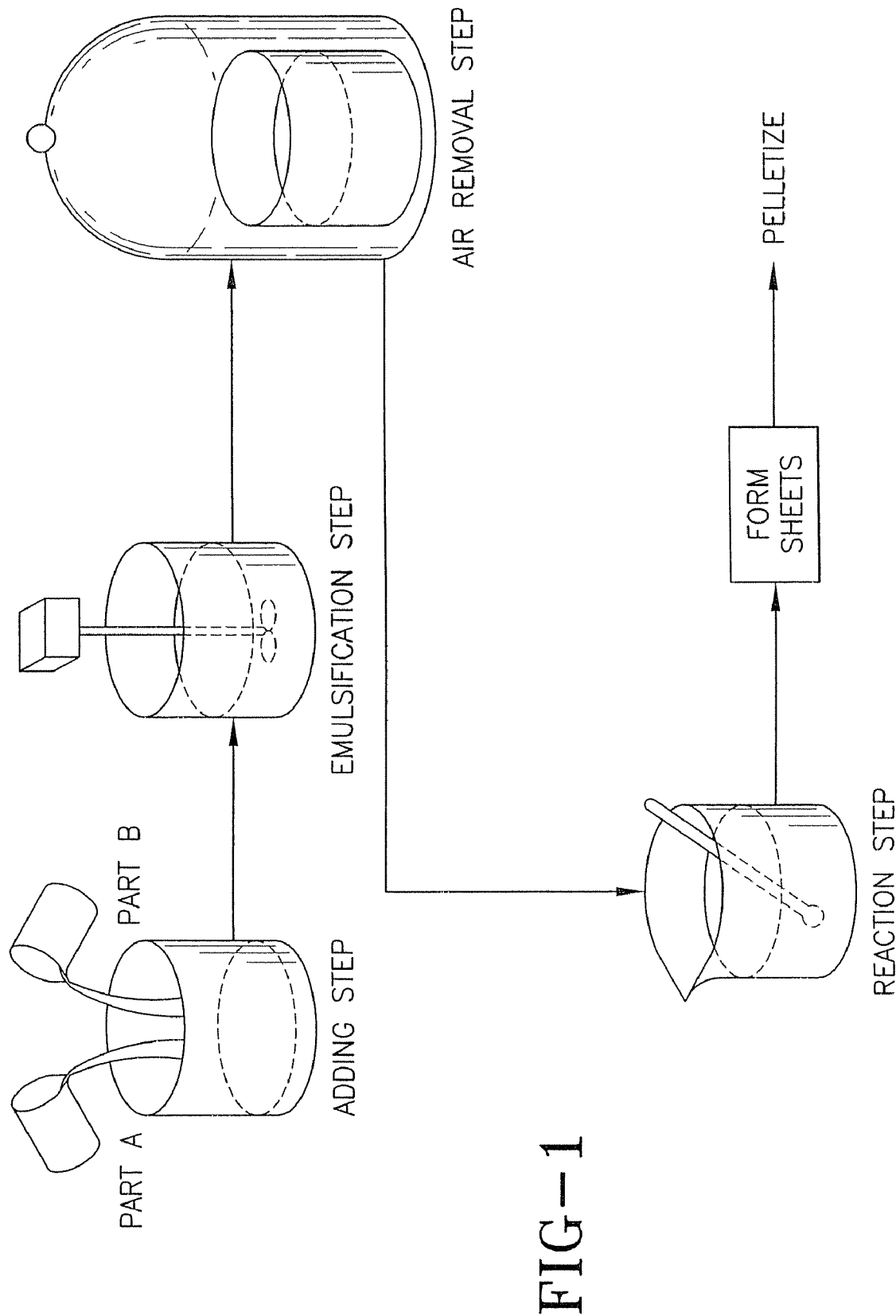
FIG. 1 is a diagram of a process for making an embodiment of the invention.

The present invention is directed to a coating of a hard material on the surface of a soft material. The product, which is preferably, tubing or film, a multilayered article that has soft characteristics for flexibility, patient comfort and ease of clamping to control the flow of fluids. For medical grade tubing, the product preferably has good bonding properties and minimizes risk of exposing a patient to substances that can migrate from the tubing to medical fluids, such as blood, saliva, etc.

In one embodiment, the hard material, or coating, and soft material are polymers that are characterized as essentially linear, segmented, aliphatic polyurethane elastomers. This family of polymers, being aliphatic and polyether or polycarbonate-based with 100% urethane linkages in the molecular backbone, exhibit superior flexural life and outstanding hydrolytic stability. In addition, the polymers can be pelletized and extruded to form a variety of shaped devices.

In one embodiment, the soft material is a soft/tacky polyurethane. Soft grades of polyurethane alone are tacky. Tacky materials are difficult to handle and they stick together and to other materials, such as packaging. Tacky materials are difficult to separate, especially when clamped, and are difficult to move passed each other and passed other materials. When the tacky materials are warm, the tack points create optical defects. These defects may effect the performance of the product. However, with a hard material, such as polyurethane coating, placed on the soft material, such as polyurethane, the problems associated with tacky materials diminish.

Basic polyurethanes are reaction products of at least one polyol, which can be a polyether, polycarbonate or polyester, with a diisocyanate or polyfunctional isocyanate material. Typically, a polyurethane has three basic building blocks: a polyol, a diisocyanate and a chain extender. Polyurethane polymers contain hard segments and soft segments, which gives it rubbery properties. The soft segment is made up of the polyol, while the hard segment is made up from the diisocyanate and the chain extender. The hardness of the polyurethane can be adjusted by the amount of the reactants used to make the polyurethane. Greater amounts of polyol will give softer materials while greater amounts of diisocyanate and chain extender give harder materials. The polyol used in this invention is preferably a polycarbonate glycol, such as polycarbonate diol or a polyether diol.

Hydroxyl terminated polycarbonates can also be used as the polyol for the polyurethanes of this invention. Molecular weight (Mn) of the polycarbonate polyol can vary from about 500 to about 10,000 but in a preferred embodiment, it will be in the range of about 500 to about 2,500. When polycarbonate is used as the polyol, the resulting polyurethane is referred to as a polycarbonate polyurethane. The hydroxyl terminated polycarbonate polyol can be prepared by reacting a glycol with a carbonate. U.S. Pat. No. 4,131,731 discloses hydroxyl terminated polycarbonates and their preparation.

Hydroxyl terminated polyether polyols are derived from a diol or polyol having a total of from 2 to 15 carbon atoms, preferably an alkyl diol or glycol which is reacted with an ether comprising an alkylene oxide having from 2 to 6 carbon atoms, typically ethylene oxide or propylene oxide or mixtures thereof. For example, hydroxyl functional polyether can be produced by first reacting propylene glycol with propylene oxide followed by subsequent reaction with ethylene oxide.

Primary hydroxyl groups resulting from ethylene oxide are more reactive than secondary hydroxyl groups and thus are preferred. Useful commercial polyether polyols include poly (ethylene glycol) comprising ethylene oxide reacted with ethylene glycol, poly(propylene glycol) comprising propylene oxide reacted with propylene glycol, poly(tetramethyl glycol) comprising water reacted with tetrahydrofuran (PTMG). Polytetramethylene ether glycol (PTMEG) is the preferred polyether polyol. Polyether polyols further include polyamide adducts of an alkylene oxide and can include, for example, ethylenediamine adduct comprising the reaction product of ethylenediamine and propylene oxide, diethylenetriamine adduct comprising the reaction product of diethylenetriamine with propylene oxide, and similar polyamide type polyether polyols. Copolyethers can also be utilized in the current invention. Typical copolyethers include the reaction product of THF and ethylene oxide or THF and propylene oxide. These are available from BASF as Poly THF B, a block copolymer, and poly THF R, a random copolymer. The various polyether polyols generally have a number average molecular weight (Mn), as determined by assay of the terminal functional groups which is an average molecular weight, of from about 500 to about 10,000, desirably from about 500 to about 5,000, and preferably from about 700 to about 3,000.

The diisocyanate is an isocyanate compound with the functionality of two isocyanates. Exemplary aliphatic diisocyanates include hexamethylene diisocyanate (HDI), isophorone diisocyanate (IPDI), trimethyl hexamethylene diisocyanate (TMHDI), dicyclohexyl methane diisocyanate (HMDI), and dimer acid diisocyanate (DDI). The diisocyanate is preferably HMDI.

Suitable chain extenders are lower aliphatic or short chain glycols having from about 2 to about 10 carbon atoms and include for instance ethylene glycol, diethylene glycol, propylene glycol, dipropylene glycol, 1,4-butanediol, 1,6-hexanediol, 1,3-butanediol, 1,5-pentanediol, 1,4-cyclohexanedimethanol hydroquinone di(hydroxyethyl)ether, neopentylglycol, and the like. The preferred chain extender is 1,4-butanediol. The mechanical properties of the polyurethane tend to change with changes in molecular weight, intermolecular forces, and building blocks of the polyurethane. The ratio of polyol to diisocyanate generally determines the hardness of the polyurethane. Preferably, the soft and tacky polyurethanes have a Shore durometer of from about 40A to about 95A, preferably from about 65A to about 85A, and the hard polyurethanes have a Shore durometer of from about 95A to about 85D, preferably from about 40D to about 75D. The durometers are determined by ASTM D2240. If a polycarbonate aliphatic polyurethane is used as the hard layer, a slightly lower Shore hardness may be used than when a polyether aliphatic polyurethane is used. When a polycarbonate aliphatic polyurethane is used as the hard layer, the Shore hardness of the hard layer will be from about 70A to about 80D, preferably from about 95A to about 60D. Polycarbonate polyurethanes are not as tacky as polyether polyurethanes and therefore less hardness is required in the polycarbonate polyurethane to remove the tack problem.

Other chemical, mechanical, and biological properties of the soft material and the hard material include high tensile strength, high ultimate elongation, good biocompatibility, high abrasion resistance, good hydrolytic stability, capability of sterilization with ethylene oxide and gamma radiation, retention of elastomeric properties at low temperature, and good melt processing characteristics for extrusion, injection molding, and other processes. Exemplary polyurethanes include thermoplastic polyurethanes, available from Thermedics Polymer Products and commercially available as Tecoflex® polyurethanes, Tecothane® polyurethanes, and Carbothene® polyurethanes. Other ingredients may be added to the polyurethane polymers used in this invention. Such other ingredients can include catalysts, antioxidants, lubricants, tinting agents, and the like as are well known to those skilled in the art. Preferably, the other ingredients are added to the reactants before the reaction occurs to form the polyurethane.

The polyurethanes may be synthesized to range from very hard to soft to tacky. The polyurethanes may be manufactured by reacting a hydroxyl group of the polyol, or polycarbonate glycol, with an isocyanate group of the diisocyanate component and the other isocyanate group of the diisocyanate with a terminal hydroxyl or amine group of the chain extender. In one embodiment, the polymerization is carried out in the presence of a solvent. In another preferred embodiment, the polymerization involves a bulk polymerization process. In the bulk polymerization process, all of the raw materials are melted and placed in a reactor, where the reaction is initiated with the addition of isocyanate. The polymerization takes place in the presence of a difunctional hydroxyl compound.

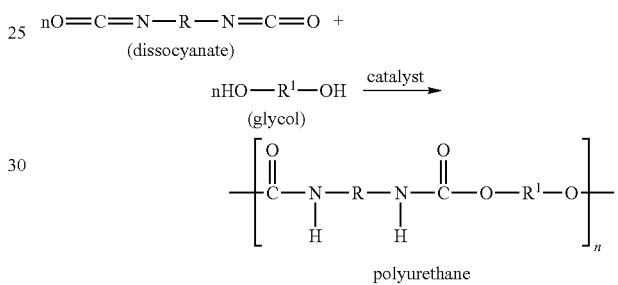

For example, as shown in FIG. 1, the polyurethane may be prepared from two components, which can be referred to as part A and part B. Part A is the aliphatic diisocyanate. Part B is comprised of the polyol, the glycol chain extender, a catalyst, an antioxidant, and a lubricant. The proper stoichiometric proportions of part A and part B are emulsified by a mixer at room temperature to form a moderately reactive thixotropic mixture having a viscosity below about 2500 cps. Since the emulsification introduces air into the reactive mixture, the air must be removed. The air bubbles are removed by placing a vessel containing the emulsion under a bell jar and evacuating the air from the bell jar with a suction device. The bell jar is evacuated to a pressure of about 0.3 microns and the mixture is kept under the bell jar about 8 minutes causing the mixture to appear to boil. After the emulsion is taken from the bell jar, it is allowed to stand until the exothermic reaction that is taking place brings it to a temperature of about 40° C.

At this point, the emulsion is preferably poured into a pan where it is allowed to flow to form uncured sheets. The pan with the sheets is then placed in an oven and heated at a temperature of at least 110° C. for four hours or more until the elastomer is cured. The sheets are then chopped up or pelletized in a standard pelletizer resulting in pellets approximately ¼ inch in length. These pellets are then used in machinery suitable for an extrusion of the desired product. Alternatively, the pellets may be dissolved in a solvent, such as dimethyl acetamide, tetrahydrofuran, 1,4 dioxane and m-pyrrol. The solution may then be used to make an article by a solvent casting method. These methods are further described in U.S. Pat. No. 4,447,590, the entire content of which is hereby incorporated by reference.

The hard material (e.g., polyurethane) coating decreases tubing chemical susceptibility (solvent attack), cosmetic defects found with the soft extruded materials, and tack found with the soft material. The coating of hard material (e.g., polyurethane) improves the strength of the tube, decreases drug interactions with the tube, and improves biocompatibility of the tube surfaces. The coating also allows the use of soft/tacky material (e.g., polyurethane) without any additives that would reduce the tack through chemistry.

In particular, at least the fluid contacting surfaces of the tubing contain no phthalate or citrate esters or other plasticizers, which are capable of leaching into pharmaceutical fluids. Blood clotting, rejection responses, and tissue inflammation are minimized. The polymeric blends, tubing, and tubing assemblies also preferably avoid absorption of solvents, drugs, pharmaceutical agents and other materials that come in contact with them. The polyurethanes of this invention pass biocompatibility and biostability testing.

To demonstrate the biocompatibility of the aliphatic polyurethanes used in this invention, the following tests are used:

| Test | Procedure |
| --- | --- |
| Minimum Essential Medium (MEM) Elution | ISO 10993 - Part 5, (1999); Tests for in vitro cytotoxicity |
| Indirect Hemolysis | ISO 10993 - Part 4, (1992); Selection of tests for interactions with blood |
| In Vitro Hemocompatibility | ISO 10993 - Part 4, (1992); Selection of tests for interactions with blood |
| Systemic Injection Study | ISO 10993 - Part 11 (1993); Tests for systemic toxicity; Extraction procedures were based on ISO Standard 10993-12 (1996) |
| Intracutaneous | ISO 10993 - Part 10 (1995); Tests for irritation and sensitization tests; Extraction procedures were based on ISO Standard 10993-12 (1996) |
| Pyrogen | ISO 10993 - Part 11, (1993); Tests for systemic toxicity; Extraction procedures were based on ISO Standard 10993-12. (1996) |
| Physiochemical Test for Plastics | United States Pharmacopoeia 24, National Formulary 19, pp. 1932-1933, 2000. |

To demonstrate the biostability of the aliphatic polyurethanes used in this invention, the test used was the Implantation test, 2-week histopathology. The test was conducted in accordance with ISO Standards 10993—Part 6 (1994); tests for local effects after implantation.

The hard and soft layers of the articles made according to this invention both pass all of the above listed tests for biocompatibility and biostability. This is an important feature of this invention. Since the end use products, such as tubing, of this invention are to be used in medical applications, it is important that they exhibit biocompatibility and biostability.

Figure 3:
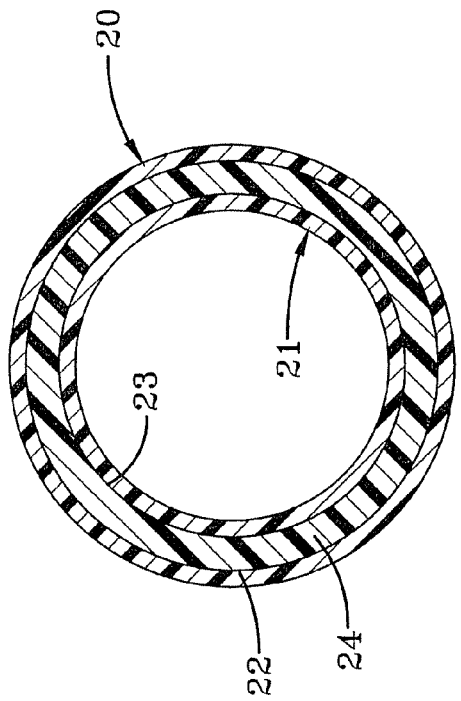
FIG. 3 is a cross-sectional view of a second embodiment of the invention showing a tube with an outer layer and inner layer of hard polyurethane with a layer of soft polyurethane between the two hard layers.
Figure 5:
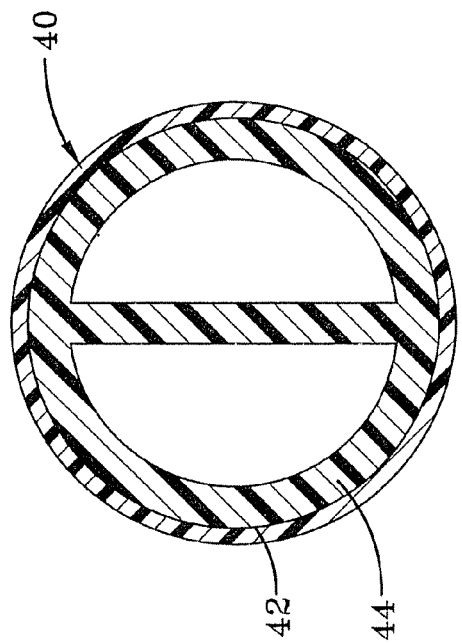
FIG. 5 is a cross-sectional view of a fourth embodiment of the invention showing a profile tube having an outer layer of hard polyurethane and an inner layer of soft polyurethane.
Figure 2:
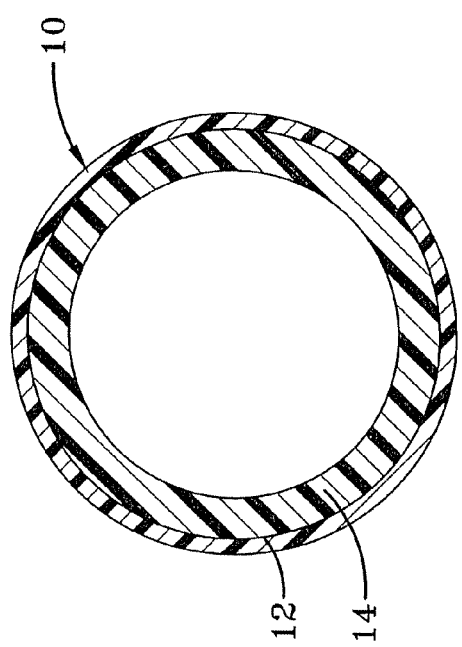
FIG. 2 is a cross-sectional view of a first embodiment of the invention showing a tube with an inner layer of soft polyurethane and an outer layer of hard polyurethane.
Figure 4:
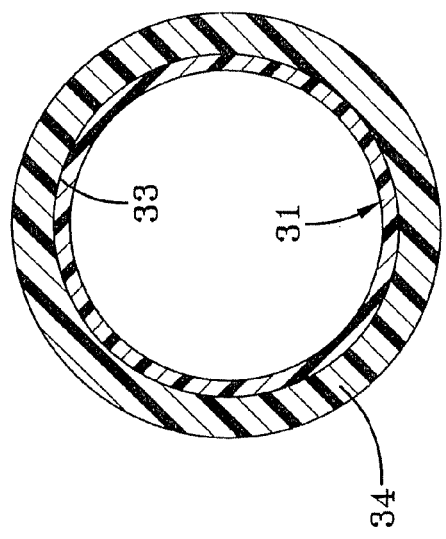
FIG. 4 is a cross-sectional view of a third embodiment of the invention showing a tube with an inner layer of hard polyurethane and an outer layer of soft polyurethane.

The hard material (e.g., polyurethane) can be placed on the outer surface, the inner surface or both surfaces of the soft material (e.g., polyurethane). For example, FIG. 2 shows a device, such as medical tubing, having a hard material 10 on an outer surface 12 of a soft material 14, FIG. 3 shows coatings 20 and 21 placed on an outer surface 22 and inner surface 23, respectively, of a soft polyurethane 24. The inner and outer hard coating materials may be the same materials, similar materials, or different materials. FIG. 4 shows a hard coating 31 placed on an inner surface 33 of a soft polyurethane 34. Although FIGS. 2-4 show the coatings on a round device, the device may be of any shape and size. For example, the tubing may be a profile tube, as shown in FIG. 5, where a coating 40 is placed on an outer surface 42 of a soft polyurethane 44.

In addition, the hard materials may be placed on other medical devices, as well as non-medical devices that contain tacky materials. For example, the hard material may be placed on piping used as process lines in aqueous systems, such as water treatment systems, potable and non-potable water supply lines, low pressure feed lines, exhaust lines, water or aqueous discharge lines, gas vents, conduit for dry solids, underground conduit for wiring, and overhead conduit and on piping used in secondary containment systems, sewer lining systems, irrigation systems, production wells, monitoring wells, injection wells, leachate collection systems, and sprinkler systems. The coating may also be used on sheeting, including stockpile covers (e.g., cover contaminated soils to prevent rainwater from infiltrating soils and groundwater), pond, container, and lagoon liners, truck bed liners, dump truck covers, foundation liners, boots for sealing piping with other structures, barriers in slurry walls, and dust control enclosures and grids and mesh, including geo-grids for soil stabilization, temporary fencing, sacrificial layer in underground utilities, wick drains, filter applications such as in soil collection systems, and silt fence. Further applications include drums, lids, and other containers, temporary dam structures, concrete form for underwater applications, pontoons and other buoyancy devices, and disposable boots and boot liners, gloves, and sampling devices.

The hard material improves handling of the article and is placed on the article in a thickness not to effect the soft characteristics of the article. The thickness of the coating must be large enough to reduce the surface tack, but small enough to not significantly change the stiffness of the article. In one embodiment, the thickness of the coating ranges from about 0.0001 to 0.010 inches, depending on the size of the tube. For example, for a tube with a 0.025 inch wall, the preferred coating thickness is about 0.0005 to 0.001 inches. For larger tubes, the thickness of the hard material could be thicker than 0.001 inches.

In one embodiment, processing of the materials is performed under common coextrusion techniques. Coextrusion is a polymer processing method for bringing different polymeric materials together to form unitary layered structures, such as films, sheets, fibers, and tubing. This allows for unique combinations of materials, and for structures with multiple functions, such as, barrier characteristics, radiation resistance, and heat sealability. In coextrusion processes, different extruders are used for each different material used in making the desired article. For example, if two materials are used, such as a soft and hard polyurethane, two extruders would be used. The melt streams are brought together to form the coextruded final article. The materials are brought together hot in the coextrusion process and are melt bonded together. If three materials are used, then three extruders would be used, and so forth. The shape and/or thickness of the coextruded layers depends upon the efficiency of the particular extrusion equipment utilized. Coextrusion may also be combined with blown film processing so that film structures can be made with no inherent waste and much lower capital investment over flat film coextrusion. However, flat film processing techniques provide an excellent method for making multilayered structures. Film made according to this invention can be fabricated into containers, such as blood and IV bags by heat sealing the film.

Component polymer or copolymer materials according to the present invention can be coextruded from the melt state in any shape, which is rapidly cooled to obtain a multilayered structure. The shape and/or thickness of the coextruded structure will be dependent upon the efficiency of the particular extrusion equipment employed and the quenching systems utilized. Generally, films and tubes are the preferred coextruded structures.

The components are thoroughly mixed prior to being charged to the extruder (e.g., pellets of the individual materials are blended together prior to being charged into the extruder where they are further mixed by the extruder and extruded). Alternatively, the materials may be individually metered into the extruder in the correct proportion. The pellets should be dried to a moisture content of 0.05% or less prior to extruding.

In one embodiment, once the tubing has been extruded in appropriate lengths and sizes, tubing assemblies may be formed by bonding these lengths to one or more plastic fluid transporting components. For tubing, the sizes may range from about 0.003 inch inner diameter (ID)×about 0.011 inch outer diameter (OD) to about 0.500 inch ID×about 0.550 inch OD. Preferably, the OD ranges from about 0.06 inches to about 0.2 inches with a wall thickness of about 0.01 to 0.03 inches. The length may be about 0.125 inches or longer.

The preferred dies used to manufacture coextruded tubing are generally commercially available, i.e., Genca in Clearwater, Fla. However, any available dies may be used. The standard extrusion conditions for the materials of interest will work for this application.

REPRESENTATIVE EXAMPLE

To co-extrude a tube as shown in FIG. 2, the soft layer 14 is an aliphatic polyurethane having a Shore Hardness of 80A and the hard layer 10 is an aliphatic polyurethane having a Shore Hardness of 60D. Both the soft and hard polyurethanes are extrusion grade and are commercially available as Tecoflex® from Thermedics Polymer Products in Wilmington, Mass., U.S.A. Prior to extruding, the pellets of the soft and hard polyurethanes are dried to a moisture content of 0.05% or less. Two extruders are used, a 1 inch extruder for the hard layer and a 1½ inch extruder for the soft layer. Each extruder has 4 heat zones. The extruder heat zone temperatures and conditions for the soft layer is as follows:

Zone 1 - 330° F. ± 25° F.
Zone 2 - 340° F. ± 25° F.
Zone 3 - 350° F. ± 25° F.
Zone 4 - 360° F. ± 25° F.
Melt Temp. - 360° F. ± 25° F.
Die Temp. - 360° F. ± 25° F.
Pressure - 1,000-2,500 psi
Screen Pack - 500 mesh The extruder heat zone temperatures and conditions for the hard layer is as follows:

Zone 1 - 360° F. ± 25° F.
Zone 2 - 370° F. ± 25° F.
Zone 3 - 380° F. ± 25° F.
Zone 4 - 390° F. ± 25° F.
Melt Temp. - 390° F. ± 25° F.
Die Temp. - 390° F. ± 25° F.
Pressure - 2,000-4,000 psi
Screen Pack - 500 mesh The pellets of the soft and hard polyurethane layers are fed to their respective extruder and coextruded into a tube shape using a commercially available die from Genca in Clearwater, Fla., U.S.A. The coextruded tube is cooled and wound into a roll.

If harder of softer materials are used for the two layers, the recommended extrusion temperatures will need to be adjusted, as is well known to those skilled in the art of extrusion. Usually, for a harder polyurethane, the extrusion temperature is adjusted higher and for a softer polyurethane, the extrusion temperature is adjusted lower.

The individual layers of the tube pass biocompatibility and biostability testing.

In addition, coating could be added by common solution cast methods. In one example of a common solution cast method, 10 grams of hard polyurethane are dissolved in 500 grams of tetrahydrofuran. Dimethyl acetamide, cyclohexanone, cyclopentanone, dimethyl formamide, methylene chloride, or dioxane may also be used. The solution is placed into a dipping tank and the tubing is attached to an apparatus to dip the tubing. At a controlled rate (for example, 20 inches/minutes), the tube is dipped into the solution and retracted. The excess solvent is allowed to drip off the tube and the solvent is evaporated.

Tubing and tubing assemblies according to the present invention can be utilized in a wide range of both medical and non-medical products. In the medical area, the tubing and tubing assemblies are suitable for replacing chlorine-containing PVC tubing, such as is utilized with IV fluid administration sets, infusion sets, cassettes, arthroscopy fluid control systems, cardiovascular systems and blood gas monitoring systems.

While the invention has been described in detail and with reference to specific embodiments thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents.

What we claim is:

1. A process for making a multilayer tube comprising:
   providing a hard aliphatic polyurethane selected from the group consisting of polyether polyurethane and polycarbonate polyurethane having a Shore hardness from about 95A to about 85D as measured according to ASTM D2240, with the proviso that if said aliphatic polyurethane is a polycarbonate polyurethane, said Shore hardness of said hard aliphatic polyurethane is from about 70A to about 80D, and a soft aliphatic polyether polyurethane having a Shore hardness from about 40A to about 95A as measured according to ASTM D2240;
   coextruding said soft aliphatic polyurethane and said hard aliphatic polyurethane to form a multilayer tube; wherein both of said soft aliphatic polyurethane and said hard aliphatic polyurethane are biocompatible and biostable.

2. The process of claim 1, wherein said hard aliphatic polyurethane has a Shore hardness of from about 40D to about 75D, and wherein said soft aliphatic polyurethane has a Shore hardness of from about 65A to about 85A.

3. The process of claim 1, wherein said tube has a thickness of said hard aliphatic polyurethane of from about 0.0005 to about 0.001 inch.

* * * * *